US00PP33264P2

(12) United States Plant Patent
Van Swieten

(10) Patent No.: US PP33,264 P2
(45) Date of Patent: Jul. 13, 2021

(54) ***PHALAENOPSIS* PLANT NAMED 'PHALINYFA'**

(50) Latin Name: *Phalaenopsis* *hybrid*
Varietal Denomination: PHALINYFA

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,006

(22) Filed: Feb. 3, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALINYFA', particularly characterized by light yellow-green and flecked flowers with red-purple, dotted lips, a convex flower shape in lateral view, dotted apical lobes of the lip, and is propagated by meristem tissue culture, is disclosed.

3 Drawing Sheets

Genus and species: *Phalaenopsis* hybrid.
Variety denomination: 'PHALINYFA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALINYFA'.

The new *Phalaenopsis* plant is a product of a planned breeding program conducted by the inventor in Bleiswijk, the Netherlands. The objective of this breeding program was to create a new *Phalaenopsis* plant with numerous attractive light yellow-green, flecked flowers with red-purple, dotted lips, suitable for potted plant production.

The new *Phalaenopsis* plant 'PHALINYFA' is a result of cross-pollination made by the inventor in June 2012 in Bleiswijk, the Netherlands, of the proprietary female, or seed parent, *Phalaenopsis* hybrid '40949-011' (unpatented) with the proprietary male, or pollen parent, *Phalaenopsis* hybrid '6240-02' (unpatented).

The new *Phalaenopsis* was selected by the inventor as a single plant within the progeny of the stated cross-pollination in a controlled greenhouse in Bleiswijk, the Netherlands, in May 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 19, 2019 (Application no. 2019/2293), by Applicant who obtained the subject matter disclosed directly from the inventor. 'PHALINYFA' has not been made publicly available or sold anywhere in the world prior to the effective filing date of this application with the exception of sales or disclosures made one year or less before the effective filing date of this claimed invention by Applicant who obtained 'PHALINYFA' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALINYFA' as a new and distinct variety of *Phalaenopsis* plant:

1) Light yellow-green and flecked flowers with red-purple, dotted lips;
2) Flower shape in lateral view is convex; and
3) Apical lobe of the lip is dotted.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in December 2020. Colors in the photographs may differ from the color values cited in the detailed botanical description, which accurately describe the actual colors of the new variety.

DESCRIPTION OF THE NEW VARIETY

Figure 1:
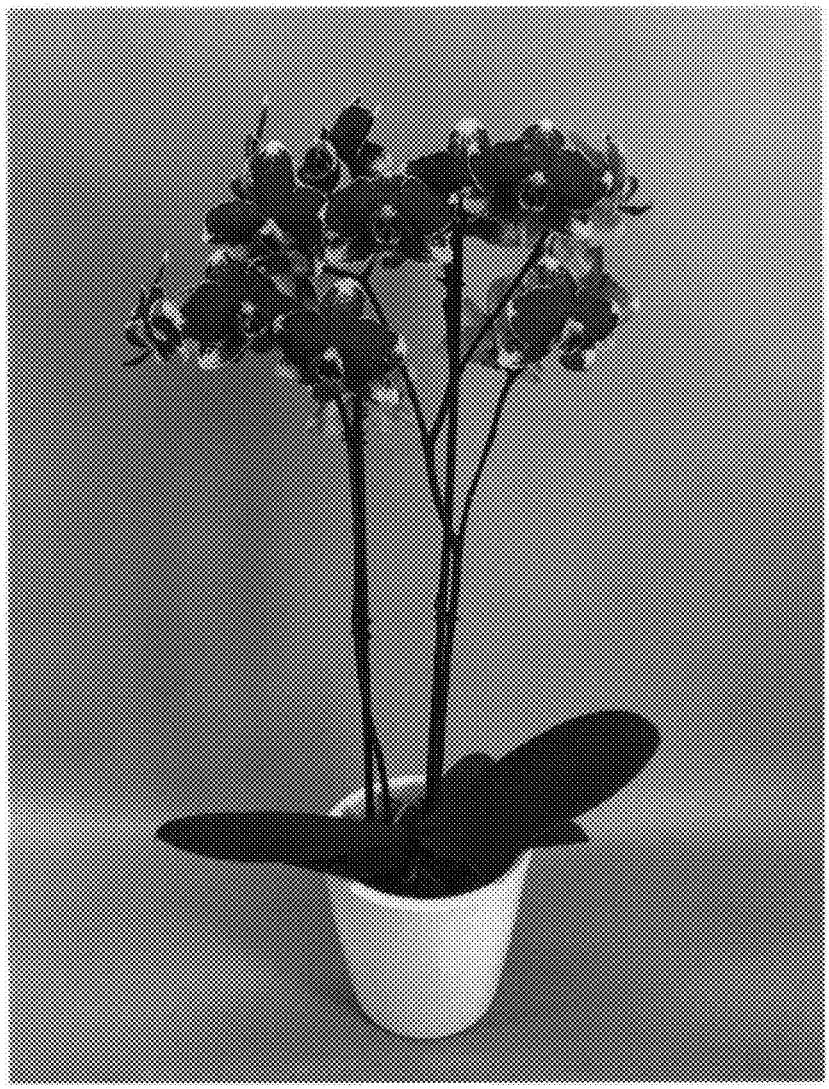
FIG. 1 shows the overall plant habit, including blooms and foliage of 'PHALINYFA'.
Figure 2:
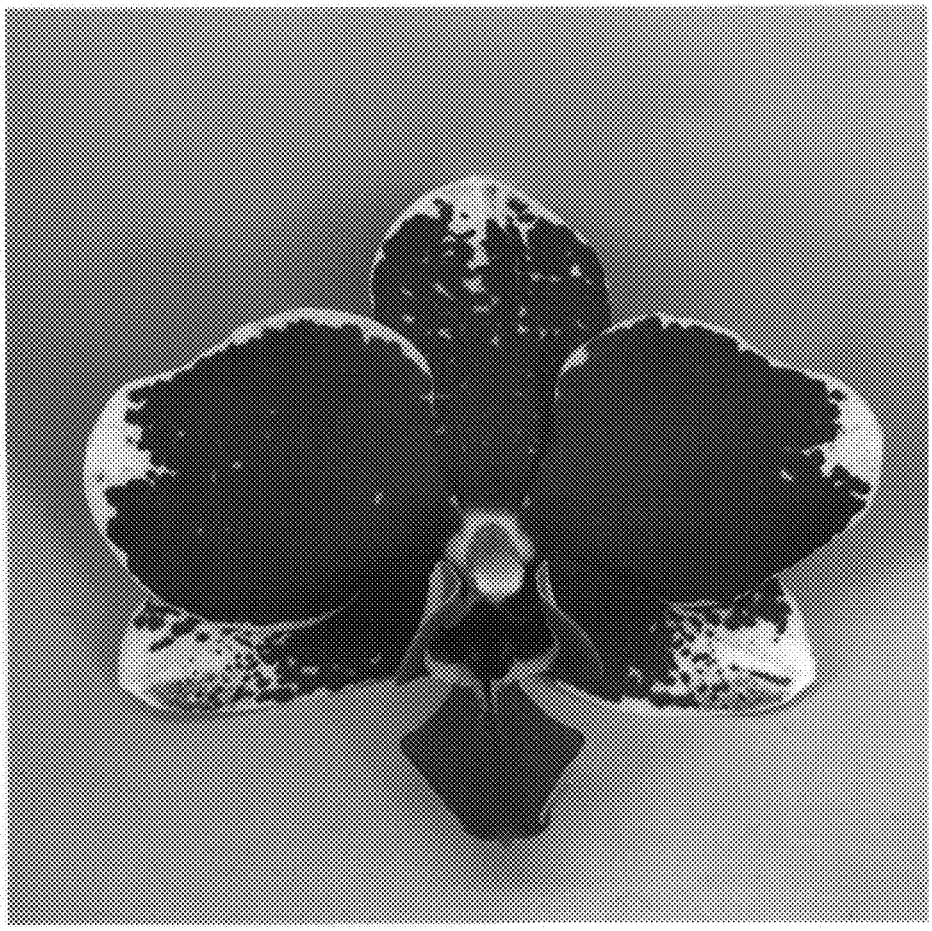
FIG. 2 shows a close-up of a flower of 'PHALINYFA'.
Figure 3:
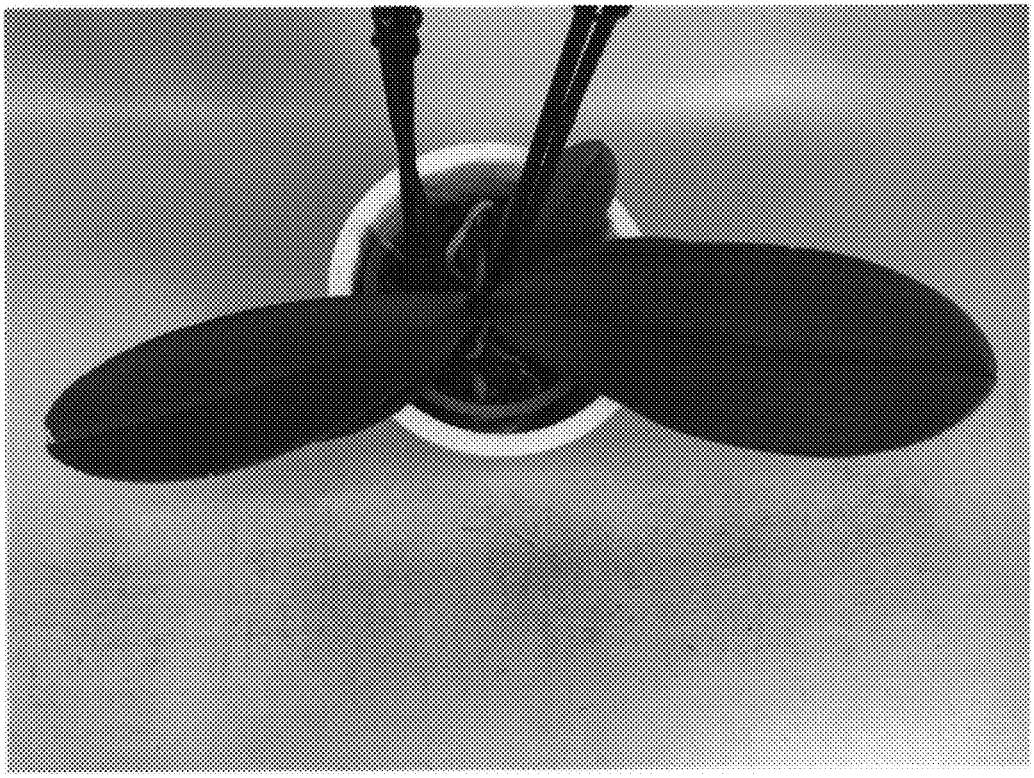
FIG. 3 shows an overhead view of the leaves of 'PHALINYFA'.

The following detailed description sets forth the distinctive characteristics of 'PHALINYFA'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in December 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALINYFA'.

Parentage:

*Female parent*.—*Phalaenopsis* cultivar '40949-011' (unpatented).

*Male parent*.—*Phalaenopsis* cultivar '6240-02' (unpatented).

Propagation:

*Type*.—Meristem tissue culture.

Roots:

*Root description*.—Greyed-green (something in between RHS 190B and 190C) colored roots with branching lateral roots having yellow-green (RHS 144C) colored root tips with a touch of purplish-red (RHS N77B).

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 44.0 cm to 49.0 cm.

*Width* (*measured from leaf tips*).—About 28.0 cm to 31.0 cm.

*Vigor*.—Moderate.

Leaves:

*Mature leaves*.—Quantity per plant: 6 to 8 leaves are produced before flowering. Length (fully expanded): 15.0 cm to 18.0 cm. Width: 6.0 cm to 7.0 cm. Shape: Oblong. Base shape: Moderately elongated. Apex: Obtuse slightly unequal. Leaf blade angle with the petiole (measured from the horizontal position): Between 15 degrees and 30 degrees. Leaf margin: Entire. Color: Upper surface: RHS 146A and diluting reddish-brown margin (RHS 200B) toward the tip. Lower surface: RHS 146B and diluting dark red-brown region and margin (something in between RHS 187A and 200B) toward the tip. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B with a touch of diluting dark red (RHS 187A) toward the tip.

Peduncle:

*Quantity per plant*.—1 to 2.

*Number of flowers per peduncle*.—8 to 15.

*Length*.—44.0 cm to 49.0 cm.

*Diameter*.—4.0 mm to 5.0 mm.

*Strength*.—Strong.

*Aspect*.—Upright to slightly pendent.

*Texture*.—Smooth.

*Color*.—Reddish-brown (RHS 200B) with a touch of yellow-green (RHS 146C).

*Internode length*.—4.0 cm to 5.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 2.

*Inflorescence size*.—Height (from base to tip): 170.0 mm to 270.0 mm.

*Flowering time*.—First flowers can be expected 10 to 11 months after planting in a 12-cm pot.

*Flower*.—Height: 70.0 mm to 75.0 mm. Diameter: 80.0 mm to 85.0 mm. Depth of lip: 22.0 mm to 24.0 mm. Flower shape: Convex.

*Flower longevity*.—On the plant: 17 to 20 weeks.

*Fragrance*.—Absent.

*Flower bud*.—Average size: Medium to large. Length: 21.0 mm to 23.0 mm. Width: 16.0 mm to 18.0 mm. Shape: Egg shaped. Color: Yellow-green (something in between RHS N144A and 144C) with a touch of dark red (something in between RHS 187B and 187C).

*Petals*.—Arrangement: Open/free. Shape: Semi-circular. Apex: Obtuse asymmetric. Margin: Moderately undulated. Length (from base to tip): 38.0 mm to 40.0 mm. Width: 36.0 mm to 38.0 mm. Position of the broadest part of the petal: At the base. Color (when fully opened): Upper surface: Basic color: Light yellow-green (RHS 2C). Over color: Dark purplish-red flecks (RHS N79C). Lower surface: Basic color: Greenish-yellow (RHS 2D). Over color: White (RHS NN155C) at the base; diluting purplish-red flecks (something in between RHS N77B and N79B). Number of spots, flecks, and stripes on the petals (upper surface): Many flecks. Color of spots, flecks, and stripes on the petals (upper surface): RHS N79C. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 40.0 mm to 42.0 mm. Width: 24.0 mm to 26.0 mm. Color (when fully opened): Upper surface: Basic color: Light yellow-green (RHS 2C). Over color: Dark purplish-red flecks (RHS N79C). Lower surface: Basic color: Light yellow-green (RHS 2C). Over color: Diluting purplish-red flecks (something in between RHS N77B and N79B). Number of spots, flecks, and stripes on the dorsal sepals (upper surface): Many flecks. Color of spots, flecks, and stripes on the dorsal sepals (upper surface): RHS N79C. Density of netting of the dorsal sepals (upper surface): None. Color of the netting (upper surface): Not applicable.

*Lateral sepals*.—Shape: Ovate. Apex: Obtuse asymmetric. Margin: Entire. Length (from base to tip): 39.0 mm to 41.0 mm. Width: 23.0 mm to 25.0 mm. Color (when fully opened): Upper surface: Basic color: Light yellow-green (RHS 2C). Over color: Dark purplish-red flecks on one side (RHS N79C) and other side (something in between RHS 187C and 187D). Lower surface: Basic color: Light yellow-green (something in between RHS 145C and 2C). Over color: Diluting purplish-red flecks (something in between RHS N77B and N79B) with a reddish-purple midvein (RHS N78A) toward the tip. Number of spots, flecks, and stripes on the lateral sepals (upper surface): Many flecks. Color of spots, flecks, and stripes on the lateral sepals (upper surface): RHS N79C and something in between RHS 187C and 187D. Density of netting of the lateral sepals (upper surface): None. Color of the netting (upper surface): Not applicable.

*Labellum* (*lip*).—Whiskers: Present. Length of whiskers: 5.0 mm to 8.0 mm. Color of whiskers: Dark purplish-red (RHS N79C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated (widely wavy). Length: 18.0 mm to 20.0 mm. Width: 12.0 mm to 14.0 mm. Color: Upper surface: Slightly light greenish-yellow (RHS 6B) with dark red fleck (something in between RHS 187A and 187B) at the base; white (RHS NN155A); dark red (something in between RHS 187A and 187B) on one side and dark purplish-red (RHS N79C) toward tip. Lower surface: Greenish-white (RHS 155C) at the base; hint of light yellow (RHS 6B) and dark red (something between RHS 187A and 187B) toward margin on one side and reddish-purple (RHS N78A) toward the tip. Number of spots, flecks, and stripes on the lateral lobe (upper surface): Fleck. Color of spots, flecks, and stripes on the lateral lobe (upper surface): Something in between RHS 187A and 187B. Density of netting of the lateral lobe (upper surface): None. Color of the netting (upper surface): Not applicable.

*Apical lobe*.—Shape: Rhombic. Margin: Entire. Length: 21.0 mm to 23.0 mm. Width: 18.0 mm to 20.0 mm. Color: Upper surface: Touch of greenish-yellow (RHS 6B) at the base; red (RHS 59A); dotted (something in between RHS 187A and 187B); dark red midvein (RHS 187A) and dark purplish-red (RHS N79C) toward whiskers. Lower surface: White (RHS 155C) at the middle from base toward whiskers; touch of light yellow (RHS 6B) toward wings; dark red margin at wings (RHS 187B) and reddish-purple (something in between RHS N79C and N78A) on sides toward whiskers. Number of spots, dots, and stripes on the apical lobe (upper surface): Many dots. Color of spots, dots, and stripes on the apical lobe (upper surface): Something in between RHS 187A and 187B. Density of netting of the apical lobe (upper surface): None. Color of the netting (upper surface): Not applicable. Bump and ridge: Present.

*Callus*.—Average size: Small to medium. Height: 5.0 mm to 6.0 mm. Length: 5.0 mm to 6.0 mm. Width: 4.0 mm to 5.0 mm. Color: Dark red (something in between RHS 187A and 187B) with few light yellow-green flecks (RHS 2C) at the tip.

Reproductive organs:

*Column*.—Length: 9.0 mm to 11.0 mm. Diameter: 5.0 mm to 6.0 mm. Color: Purplish-pink (RHS N78C) with few stripes (RHS N78A) at the base.

*Pollinia*.—Quantity: 2. Diameter: 0.8 mm to 1.0 mm. Color: Orange-yellow (RHS 21A).

*Ovary*.—Length: 14.0 mm to 16.0 mm. Diameter: 2.3 mm to 2.6 mm.

*Pedicel*.—Length: 39.0 mm to 41.0 mm. Diameter: 2.7 mm to 3.1 mm. Color: Green (RHS 146A) at the base; yellow-green (RHS 145C) and light purple (RHS 76A) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALINYFA' differs from the female parent plant '40949-011' (unpatented) in that 'PHALINYFA' has flowers with a flecked pattern and purplish-pink columns with few reddish-purple stripes at the base, whereas '40949-011' has flowers with an edged pattern and columns with a touch of reddish-purple at the base and light purple tips.

'PHALINYFA' differs from the male parent plant '6240-02' (unpatented) in that 'PHALINYFA' has rhombic apical lobes and weakly spatulate lateral lobes, whereas '6240-02' has triangular apical lobes and spatulate lateral lobes. Additionally, 'PHALINYFA' has smaller flowers than '6240-02'.

'PHALINYFA' is most similar to the commercial *Phalaenopsis* plants named 'PHALCHORBE' (U.S. Plant patent application Ser. No. 17/016,639) and 'PHALGOPXO' (U.S. Plant Pat. No. 32,285). 'PHALINYFA' differs from the commercial variety 'PHALCHORBE' in that 'PHALINYFA' has rhombic apical lobes and dark purplish-red whiskers, whereas 'PHALCHORBE' has triangular apical lobes and white whiskers with light yellow tips. Additionally, 'PHALINYFA' has shorter whiskers than 'PHALCHORBE'.

'PHALINYFA' differs from the commercial variety 'PHALGOPXO' in that 'PHALINYFA' has purplish-pink columns with few reddish-purple stripes at the base and dark purplish-red whiskers, whereas 'PHALGOPXO' has white columns and very light purple whiskers with yellow tips.

I claim:

1. A new and distinct variety of *Phalaenopsis* plant named 'PHALINYFA', substantially as described and illustrated herein.

* * * * *